(12) United States Patent
Baroni et al.

(10) Patent No.: US 8,501,806 B2
(45) Date of Patent: Aug. 6, 2013

(54) METHODS FOR PREVENTING OR REDUCING COLON CARCINOGENESIS

(75) Inventors: Sergio Baroni, Villa D'adda (IT);
Salvatore Bellinvia, Pordenone (IT);
Francesca Viti, Sesto San Giovanni (IT);
Giovanni Monteleone, Rome (IT)

(73) Assignee: Nogra Pharma Limited, Dublin (IE)

( * ) Notice: Subject to any disclaimer, the term of this patent is extended or adjusted under 35 U.S.C. 154(b) by 36 days.

(21) Appl. No.: 13/131,982

(22) PCT Filed: Dec. 3, 2009

(86) PCT No.: PCT/EP2009/008633
§ 371 (c)(1),
(2), (4) Date: Aug. 11, 2011

(87) PCT Pub. No.: WO2010/063472
PCT Pub. Date: Jun. 10, 2010

(65) Prior Publication Data
US 2011/0288177 A1 Nov. 24, 2011

Related U.S. Application Data

(60) Provisional application No. 61/157,674, filed on Mar. 5, 2009, provisional application No. 61/222,281, filed on Jul. 1, 2009.

(30) Foreign Application Priority Data

Dec. 5, 2008 (EP) ..................................... 08425775

(51) Int. Cl.
*A61K 31/19* (2006.01)
(52) U.S. Cl.
USPC ........................................................ 514/545
(58) Field of Classification Search
USPC ........................................................ 514/575
See application file for complete search history.

(56) References Cited

U.S. PATENT DOCUMENTS

| | | | |
|---|---|---|---|
| 3,211,610 A | 10/1965 | Rogers | |
| 3,444,232 A | 5/1969 | Bernstein | |
| 4,036,951 A | 7/1977 | Halpern et al. | |
| 4,348,223 A | 9/1982 | Grove | |
| 4,429,152 A | 1/1984 | Gries et al. | |
| 4,720,506 A | 1/1988 | Munakata et al. | |
| 4,933,330 A | 6/1990 | Jorgensen et al. | |
| 5,262,549 A | 11/1993 | Telfer et al. | |
| 5,302,751 A | 4/1994 | Manimaran et al. | |
| 5,519,014 A | 5/1996 | Borody | |
| 5,594,151 A | 1/1997 | Stolowitz | |
| 6,194,627 B1 | 2/2001 | Geissler et al. | |
| 6,326,364 B1 | 12/2001 | Lin et al. | |
| 6,583,128 B2 | 6/2003 | Ekwuribe et al. | |
| 7,098,025 B1 | 8/2006 | Auwerx et al. | |
| 7,429,676 B2 | 9/2008 | Woltering et al. | |
| 7,749,980 B2 * | 7/2010 | Plourde et al. | 514/45 |
| 8,138,357 B2 * | 3/2012 | Naccari et al. | 549/285 |
| 8,153,693 B2 * | 4/2012 | Baroni et al. | 514/567 |
| 8,153,841 B2 | 4/2012 | Naccari et al. | |
| 2003/0113815 A1 | 6/2003 | Houseknecht et al. | |
| 2003/0133875 A1 | 7/2003 | Kelly | |
| 2003/0220374 A1 | 11/2003 | Needleman | |
| 2003/0229083 A1 | 12/2003 | Debnath et al. | |
| 2004/0034067 A1 | 2/2004 | MacPhee | |
| 2004/0115127 A1 | 6/2004 | Wright et al. | |
| 2004/0132110 A1 | 7/2004 | Desreumaux et al. | |
| 2006/0177444 A1 | 8/2006 | Horizoe | |
| 2006/0270635 A1 | 11/2006 | Wallace et al. | |
| 2007/0149804 A1 | 6/2007 | Woltering et al. | |
| 2009/0048343 A1 | 2/2009 | Naccari et al. | |
| 2009/0118357 A1 | 5/2009 | Naccari et al. | |
| 2010/0305077 A1 | 12/2010 | Baroni et al. | |
| 2011/0105748 A1 | 5/2011 | Bhuniya et al. | |
| 2011/0152225 A1 | 6/2011 | Baroni et al. | |
| 2011/0288058 A1 | 11/2011 | Baroni et al. | |
| 2011/0288177 A1 | 11/2011 | Baroni et al. | |
| 2012/0053244 A1 | 3/2012 | Baroni et al. | |
| 2012/0053245 A1 | 3/2012 | Baroni et al. | |
| 2012/0157417 A1 | 6/2012 | Baroni et al. | |
| 2012/0316230 A1 | 12/2012 | Naccari et al. | |
| 2013/0005813 A1 | 1/2013 | Naccari et al. | |

FOREIGN PATENT DOCUMENTS

| | | |
|---|---|---|
| EP | 0055689 A1 | 7/1982 |
| EP | 0102833 A1 | 3/1984 |
| EP | 0291159 A2 | 11/1988 |
| EP | 0352826 A2 | 1/1990 |
| EP | 1285908 A1 | 2/2003 |
| EP | 1348698 A1 | 10/2003 |
| GB | 767788 A | 2/1957 |
| WO | WO-94/00135 A1 | 1/1994 |
| WO | WO-95/31194 A1 | 11/1995 |
| WO | WO-98/06387 A2 | 2/1998 |
| WO | WO-98/43081 A1 | 10/1998 |
| WO | WO-00/59866 A1 | 10/2000 |
| WO | WO-01/02388 A1 | 1/2001 |
| WO | WO-01/79153 A1 | 10/2001 |
| WO | WO-02/095393 A2 | 11/2002 |
| WO | WO-2004/073622 A2 | 9/2004 |
| WO | WO-2005/012280 A1 | 2/2005 |
| WO | WO-2005/072113 A2 | 8/2005 |
| WO | WO-2005/084658 A1 | 9/2005 |
| WO | WO-2006/072175 A1 | 7/2006 |
| WO | WO-2007/010514 A2 | 1/2007 |

(Continued)

OTHER PUBLICATIONS

Ahnfelt-Ronne, Ian, et al. (1990) "Clinical Evidence Supporting the Radical Scavenger Mechanism of 5-Aminosalicylic Acid," Gastroenterology, 98: 1162-1169.

(Continued)

*Primary Examiner* — Raymond Henley, III
(74) *Attorney, Agent, or Firm* — Goodwin Procter LLP

(57) ABSTRACT

The present invention is directed in part to methods of preventing or reducing colon carcinogenesis comprising administering to a patient at risk of colorectal cancer, a pharmaceutical preparation comprising a chemopreventive agent disclosed herein.

17 Claims, 11 Drawing Sheets

FOREIGN PATENT DOCUMENTS

| | | |
|---|---|---|
| WO | WO-2007/010516 A2 | 1/2007 |
| WO | WO-2008/104557 A1 | 9/2008 |
| WO | WO-2009/080828 A2 | 7/2009 |
| WO | WO-2010/063470 A2 | 6/2010 |
| WO | WO-2010/063472 A1 | 6/2010 |
| WO | WO-2010/091892 A2 | 8/2010 |
| WO | WO-2010/091894 A2 | 8/2010 |

OTHER PUBLICATIONS

Allgayer, H. (2003) "Review Article: Mechanisms of Action of Mesalazine in Preventing Colorectal Carcinoma in Inflammatory Bowel Disease," Aliment Pharmacol. Ther., 18 (Suppl. 2): 10-14.

Baker, B.R., et al., "Potential Anticancer Agents. LXXVIII Nonclassical Antimetabolites. IV. Synthesis of Compounds Related to 4-(Iodoacetamido) Salicylie Acid, an Exo-Alkylating Irreversible Inhibitor," Journal of Organic Chemistry, vol. 27 (1962) p. 3283-3295.

Beilstein Database Beistein Institute zur Forderung der Chemischen Wissenschaften, Frankfurt an Main, DE XP002413839, Accession No. 2092096, J. Med. Chem., 22: 589 (1979).

Beilstein Database, Beilstein Institute for Organic Chemistry, Frankfurt an Main, DE, retrieved from XFIRE, Accession No. brn 2208094, J. Am. Chem. Soc., 68: 2335, 2338 (1946).

Beilstein Database, Beilstein Institute for Organic Chemistry, Frankfurt an Main, DE, retrieved from XFIRE, Accession No. brn 2803076, J. Org. Chem., 14: 1013, 1018 (1949).

Beilstein Database, Beilstein Institute for Organic Chemistry, Frankfurt an Main, DE, retrieved from XFIRE, Accession No. brn 3199913, Chem. Ber., 46: 3978 (1913).

Beilstein Database, Beilstein Institute for Organic Chemistry, Frankfurt an Main, DE, retrieved from XFIRE, Accession No. brn 3200601, J. Chem. Soc., pp. 104, 111 (1935).

Beilstein Database, Beilstein Institute for Organic Chemistry, Frankfurt an Main, DE, retrieved from XFIRE, Accession No. brn 3268495, Justus Liebigs Ann. Chem., 463:60 (1924).

Beilstein Database, Beilstein Institute for Organic Chemistry, Frankfurt an Main, DE, retrieved from XFIRE, Accession No. brn 3296969, Chem. News J. Ind. Sci, 36: 269 (1877).

Beilstein Database, Beilstein Institute for Organic Chemistry, Frankfurt an Main, DE, retrieved from XFIRE, Accession No. pcrn 859019, U.S. Patent No. 4,429,152 A (Jan. 1984).

Beilstein Database, Beilstein Institute for Organic Chemistsry, Frankfurt an Main, DE, retrieved from XFIRE, Accession No. brn 3199917, Chem. Ber., 46: 288 (1913).

Beilstein Database, Beilstsein Institute for Organic Chemistry, Frankfurt an Main, DE, retrieved from XFIRE, Accession No. brn 3242057, Chem. Ber., 74: 500, 517 (1941).

Beilstein Database, Beistein Institut zur Forderung der Chemischen Wissenschaften, Frankfurt an Main, DE, XP002413837, Accession No. 2367395, Chem. Ber., 87: 179-181 (1954.).

Beilstein Database, Beistein Institut zur Forderung der Chemischen Wissenschaften, Frankfurt an Main, DE, XP002413838, Accession No. 2839685, J. Am. Chem Soc., 73: 903-904 (1951).

Beilstein Database, Beistein Institut zur Forderung der Chemischen Wissenschaften, Frankfurt an Main, DE, XP002413840, Accession No. 3031462, Bull Soc. Chim Belg., 61: 310-320 (1952).

Beilstein Database, Beistein Institut zur Forderung der Chemischen Wissenschaften, Frankfurt an Main, DE, XP002413842, Accession No. 3259704, Justus Liebigs Ann Chem, 429: 173 (1922).

Beilstein Database, Beistein Institut zur Förderung der Chemischen Wisssenschaften, Frankfurt an Main, DE, XP002413836, Accession No. 1869425, J. Labelled Compd Radiopharm, 44: S225-0S227 (2001).

Beilstein Database, Beisten Insstitut zur Forderung der Chemischen Wissenschaften, Frankfurt an Main, DE, XP002413843, Accession No. 3530419, Justus Liebigs Ann Chem, 429: 164 (1922).

Beilstein Database, Beisten Institut zur Forderung der Chemischen Wissenschaften, Frankfurt an Main, DE, XP002413841, Accession No. 2641495, J. Org. Chem., 27: 3283-3295 (1962).

Brown, et al., "Chimie Organique," C.R. Acad. Sc. Paris, t. 287 (1978) 287(4), 125-8.

Brunton, V.G., et al., "A Role for Epidermal Growth Factor Receptor, c-Src and Focal Adhesion Kinase in an in vitro Model for the Progression of Colon Cancer," Oncogene, 14: 283-293 (1997).

Bull, A.W., "The Role of Peroxisome Proliferator-Activated Receptor γ in Colon Cancer and Inflammatory Bowel Disease," Arch Pathol Lab Med, 127: 1121-1123 (2003).

Chao-Hsiung Lin et al : "An antibody transesterase derived from reactive immunization that utilizes a wide variety of alcohol substrates" Chem. Comm., 1998, pp. 1075-1076, XP009048652 compound 3, fig1 in combination with entries 12, 13 and 14 of table 1.

Clark, M., et al., "Validation of the General Purpose Tripos 5.2 Field," J. Comput. Chem., 10: 982-1012 (1989).

Collino, M., et al. (2006) "Modulation of the Oxidative Stress and Inflammatory Response by PPAR-gamma Agonists in the Hippocampus of Rats Exposed to Cerebral Ischemia/Reperfusion," European Journal of Pharmacology, Elsevier Science, NL, 530, 1-2, 70-80.

Database CA [Online] Chemical Abstracts Service, Columbus Ohio, US; Database Accession No. 67:50608, Abstract of Baker et al.: "Irreversible Enzyme Inhibitors. LXXXVII. Hydrophobic Bonding to dihydrofolic reductase. 9. Mode of Binding of m-aryloxyalkyl groups on, 6-diamino-1,2-dihydro-2,2-dimethyl-1-phenyl-s-triazine", (1967).

Database CA [Online] Chemical Abstracts Service, Columbus, Ohio, US, Database Accession No. 107:235800, Abstract of Cleary, et al., "Methylenecyclopropane rearrangement as a probe for free radical substituent effects.. sigma.. bul. Values for commonly encountered conjugating and organometallic groups", (1987).

Database CA [Online] Chemical Abstracts Service, Columbus, Ohio, US, Database Accession No. 118:101608, Abstract of Breuer, et al., "An efficient synthesis of ethyl 3'-aminocinnamate", (1992).

Database CA [Online] Chemical Abstracts Service, Columbus, Ohio, US, Database Accession No. 119:95018, Abstract of Yoon, et al., "Reduction of nitro compounds with borohydride exchange resin—nickel acetate", (1993).

Database CA [Online] Chemical Abstracts Service, Columbus, Ohio, US, Database Accession No. 50:52519, Abstract of Pratt, et al., "Reaction rates by distillation. VI. The etherification of benzyl and related alcohols", (1956).

Database CA [Online] Chemical Abstracts Service, Columbus, Ohio, US: Database Accession No. 96:19761, Abstract of Macek et al., "Studies on Local Anesthetics LXXIV. Basic esters of o-(m-) (alkoxymethyl)carbanilic acids", (1981).

Database CA [Online] Chemical Abstracts Service, Columbus, Ohio, US; Database Accession No. 105:25135, Abstract of Wulff, et al., "Chemistry of binding sites. VI. On the suitability of various aldehydes and ketones as binding sites for monoalcohols", (1986).

Database CA [Online] Chemical Abstracts Service, Columbus, Ohio, US; Database Accession No. 112:157479, Abstract of Joshi et al., "Catalysis by heteropoly acids: some new aspects", (1989).

Database CA [Online] Chemical Abstracts Service, Columbus, Ohio, US; Database Accession No. 121L204747, Abstract of Yang et al., "Photosolvolysis of 2-aminobenzyl alcohol in aqueous solution", (1994).

Database CA [Online] Chemical Abstracts Service, Columbus, Ohio, US; Database Accession No. 131:228419, The Decomposition of methyl hemiacetals of benzaldehyde in aqueous solution: a study of the effect of aromatic substitution, (1999).

Database CA [Online] Chemical Abstracts Service, Columbus, Ohio, US; Database Accession No. 135-180359, Abstract of Pitts et al., "Indium metal as a reducing agent in organic synthesis", (2001).

Database CA [Online] Chemical Abstracts Service, Columbus, Ohio, US; Database Accession No. 66:37529, Abstract of Minisci, et al., "Orientation in the radical amination of aromatic compounds with N-chlorodimethylamine-competition between nuclear and benzylic attack", (1966).

Database CA [Online] Chemical Abstracts Service, Columbus, Ohio, US; Database Accession No. 84:4573, Abstract of Gale, et al., "Amidomethylation of some N,N-dialkylanilines (Tscherniac-Einhorn reaction)", (1975).

Database CA [Online{ Chemical Abstracts Service, Columbus, Ohio, US, Database Accession No. 8:526, Abstract of Schepss, "Electrolytic reduction of aldehydes", (1914).

Database CA [Online} Chemical Abstracts Service, Columbus, Ohio, US, Database Accession No. 111:153586, Abstract of Gonzalez, et al., ".alpha.-Amino carbanions. A second generation formamidine for facile deprotonation leading to .alpha.-quaternary substitution", (1989).

Database CA [Online} Chemical Abstracts Service, Columbus, Ohio, US; Database Accession No. 110:194186, Abstract of Pei et al., "A Lewis acid catalyst supported by polymers-styrene-methyl methacrylate copolymer-titanium tetrachloride complex preparation and uses in organic synthesis", (1989).

Database CA [Online} Chemical Abstracts Service, Columbus, Ohio, US; Database Accession No. 49:68907, Abstract of Mann, et al., "The action of magnesium and of Grignard reagents on certain benzyl ethers. II. The action of Grignard reagents on .omicron.–, m-, and p-(methoxy-and phenoxymethyl) anilines", (1954).

Database Caplus Chemical Abstracts Service, Columbus, Ohio, US; Database Accession No. 1913: 10241, Abstract of Heller: Berichte der Deutschen Chemischen Gesellschaft (1913), 46, 280-94.

Database Caplus Chemical Abstracts Service, Columbus, Ohio, US; Database Accession No. 1949: 23214, Abstract of Tomcsik et al.: Helvetica Chimica Acta (1949), 32, 31-4.

Database Caplus Chemical Abstracts Service, Columbus, Ohio, US; Database Accession No. 1955-19868, Abstract of Mann et al.: Chemistry & Industry (London, United Kingdom) (1954) 373-4.

Database Caplus Chemical Abstracts Service, Columbus, Ohio, US; Database Accession No. 1979: 18291, Abstract of Brown et al.: "Affinity Chromatography of L-lactate dehydrogenase (LDH) on Synthetic Supports. Preparation and Immobilization of D- and L-p-aminophenyllactic Acids, New Effectors of LDH." Comptes Rendus des Seances de l'Academic des Scie.

Database Caplus Chemical Abstracts Service, Columbus, Ohio; Database Accession No. 1925: 25469, Abstract of Sherwin: "Acetylation as a Physiologic Reaction." Proceedings of the Society for Experimental Biology and Medicine (1924), 22, 182.

Database Caplus Chemical Abstracts Service, Columbus, Ohio; Database Accession No. 1967: 490291, Abstract of Deljac et al.: "Absolute Configuration of (—)-.beta.-hydroxy-.beta.-(m-hydroxyphenyl) propionic acid", Recueill des Travaux Chimiques des Pays-Bas (1967), 68(8), 765-8.

Database Chemcats [Online] Chemical Abstracts Service, Columbus, Ohio, Feb. 6, 2008, XP002591674.

Delbarre, F., et al., Chemical Abstracts, vol. 65, Columbus, Ohio, Abstract No. 93711, "Non-steroid antiinflammatory substances. I. Derivatives of the 4- and 5-aminosalicylic acids," (1964).

Deljac, A., et al., "Absolute Configuration of (—)-β-Hydroxy-β-(m)-Hydroxyphenyl)-Propionic Acid," Recueil des Travaux Chimiques des Pays-Bas 86 (1967), 765-768.

Dubuquoy, L., et al., "Impaired Expression of Peroxisome Proliferator-Activated Receptor Gamma in Ulcerative Colitis," Gastroenterology, 124: 1265-1276 (2003).

Dubuquoy, L., et al., "Role of Peroxisome Proliferator-Activated Receptor γ and Retinoid X Receptor Heterodimer in Hepatogastroenterological Diseases," The Lancet, 360: 1410-1418 (2002).

E. Fernholz et al.: "Specifically of antibody-catalyzed transesterifications using enol esters:a comparison with lipase reactions" J. Org. Chem., vol. 57, 1992, pp. 4756-4761, XP002330828.

Examination Report dated Apr. 15, 2011 for Application No. 06 766 083.7-2103 (11 pages).

Fuenzalida, K., et al., (2007) "Peroxisome Proliferator-activated Receptor Gamma Up-regulates the Bcl-2 Anti-apoptotic Protein in Neurons and Induces Mitochondrial Stabilization and Proection against Oxidative Stress and Apoptosis," The Journal of Biological Chemistry, 282,51,37006-37015.

Gampe, R.T., Jr., et al., "Asymmetry in the PPARγ/RXRα Crystal Structure Reveals the Molecular Basis of Heterodimerization Among Nuclear Receptors," Mol. Cell, 5: 545-555 (Mar. 2000).

Gerdes, J., et al., "Growth Fractions in Breast Cancers Determined in Situ with Monoclonal Antibody Ki-67," J. Clin. Pathol., 39: 977-80 (1986).

Gormin, D., "Picosecond Transient Absorption Spectra of Aminosalicylates in Confirmation of the Triple Excitation Mechanism," J. Phys. Chem, 1989, 93, p. 5979-5980.

Guo, et al., "Effect of Uyghur Compound Xipayi Kui Jie' an on the Ultrastructure of Small Intestinal Epithelial Cell in Rat Model of Ulcerative Colitis," Journal of Xinjiang Medical University (2009) 32 (7) , p. 893-894.

Harari, P.M., "Epidermal Growth Factor Receptor Inhibition Strategies in Oncology," Endocr Relat Cancer, 11: 689-708 (2004).

Harari, P.M., "Epidermal Growth Factor Receptor Inhibition Strategies in Oncology," Endocr Relat Cancer, 8: 3-9 (2001).

Husova, Libuse, et al., "Hepatopathy, coeliac disease and lymphocytic colitis," Ceska A. Slovenska Gastroenterologie A. Hepatologie—Czech and Slovak Gastroenterology and Hepatology, 61 (6) (2007), 309-313.

International Preliminary Report on Patentability for PCT/IE2006/000076 mailed on Jan. 22, 2008.

International Preliminary Report on Patentability, with Written Opinion, issued on Jan. 22, 2008, in parent PCT Application No. PCT/IE2006/000078, 9 pages.

International Search Report and Written Opinion of the International Search Authority issued on Jan. 1, 2007, in parent PCT Application No. PCT/IE2006/000078, 14 pages.

International Search Report for PCT/EP2008/068265, mailed Aug. 11, 2009, 6 pages.

International Search Report for PCT/EP2010/000935 mailed on Aug. 23, 2010.

International Search Report for PCT/EP2010/000939 mailed on Sep. 20, 2010.

International Search Report issued on Feb. 1, 2007 for PCT/IE2006/000076, 5 pages.

J. Med. Chem. 1985, 28, p. 717-727.

J. Phys. Chem, 1989, 93, p. 5979-5980.

J.W. Corse et al: "Biosynthesis of penicillins" J. Am. Chem. Soc., vol. 70, No. 9, 1948, pp. 2837-2843, XP002330829 Table II on p. 2838, 1st entry and synthetical procedure on p. 2840, right-hand column.

Jones, G., et al., "Development and Validation of a Genetic Algorithm for Flexible Docking," J. Mol. Biol., 267: 727-748 (1997).

Journal of Chemical and Engineering Data, vol. 14, No. 3, 1969, p. 388-391.

Journal of Labelled Compounds and Radiopharmaceuticals, vol. XXIX, No. 10, 1991, p. 1149-1155.

K.D. Janda et al.: "Antibody catalysis of bimolecular amide formation" J.Am. Chem. Soc., vol. 110, 1988, pp. 4835-4837, XP002330827.

Kari, C., et al., "Targeting the Epidermal Growth Factor Receptor in Cancer: Apoptosis Takes Center Stage," Cancer Res., 63: 1-5 (2003).

Koeffler, H.P., "Peroxisome Proliferator-activated Receptpr γ and Cancers," Clinical Cancer Research, 9: 1-9 (2003).

Liao, Yun-Zhang, et al., (1990) "Therapeutic Effect of Methyl 5-Aminosalicylate on Experimental Ulcerative Colitis in Rabbits," Acta Pharmacologica Sinica, 11(1): 54-56.

Mager, Von P.P., et al., "Struktur-Wirkungs-Beziehungen bei Salizylsaure- und Benzoesaurederivaten," Zbl. Pharm. 118 (1979) Heft 12, p. 1259-1275.

Mangelsdorf, D.J., et al., "The Nuclear Receptor Superfamily: The Second Decade," Cell, 83: 835-839 (Dec. 1995).

Meek, W., et al., "Carboxylation of Substituted Phenols in N,N-Dimethylamide Solvents at Atmospheric Pressure," Journal of Chemical and Engineering Data, vol. 14, No. 3, 1969, p. 388-391.

Mendelsohn, J., "The Epidermal Growth Factor Receptor as a Target for Cancer Therapy," Endocr Relat Cancer, 8: 3-9 (2001).

Misra, P., et al., "Phosphorylation of Transcriptional Coactivator Peroxisome Proliferator-Activated Receptor (PPAR)-Binding Protein (PBP). Stimulation of Transcriptional Regulation by Mitogen-Activated Protein Kinase," J. Biol. Chem., 277: 48745-48754 (2002).

Nolte, R.T., et al., "Ligand Binding and Co-Activator Assembly of the Peroxisome Proliferator-Activated Receptor-γ," Nature, 395: 137-143 (Sep. 1988).

O'Mahony, et al., (1990) Postgraduate Medical Journal, 66(773), pp. 238-241.

Osawa, E., et al., "Peroxisome Proliferator-Activated Receptor γ Ligands Suppress Colon Carcinogenesis Induced by Azoxymethane in Mice," Gastroenterology, 124: 361-367 (2003).

Peyrin-Biroulet, L., et al. (2007) "Peroxisome Proliferator-Activated Receptor Gamma Functions as an Antibacterial Factor," Journal of Crohn's and Colitis Supplements, 1(1).

Ponchant, M., et al., Synthesis of 5[125I]-Iodo-Zacopride, a New Probe for 5-HT3 Receptor Binding Sites, Journal of Labelled Compounds and Radiopharmaceuticals, vol. XXIX, No. 10, 1991, p. 1147-1155.

Reifen, Ram, et al. (2004) "5-ASA and Lycopene Decrease the Oxidative Stress and Inflammation Induced by Iron in Rats with Colitis," J. Gastroenterol, 39: 514-519.

Risérus, Ulf, et al., (2008) "Activation of Peroxisome Proliferator-activated Receptor (PPAR) Delta Promotes Reversal of Multiple Metabolic Abnormalities, Reduces Oxidative Stress, and Increases Fatty Acid Oxidation in Moderately Obese Men," Diabetes 57, NR. 2, 332-339.

Robertson D., et al., "Structure-Activity Relationships of Arylimidazopyridine Cardiotonics: Discovery and Intropic Activity of 2-[2-Methoxy-4-(methylsulfinyl)phenyl]-1H-imidazo[4,5-c]pyridine," J. Med. Chem. 1985, 28, p. 717-727.

Rousseaux, C., et al., Intestinal Anti-inflammatory Effect of 5-Aminosalicylic Acid is Dependent on Peroxisome Proliferator-Activated Receptor-γ, JEM 201(8): 1205-1215 (2005).

Schauber, Jurgen, et al. (2004) "Histone-Deacetylase Inhibitors Induce the Cathelicidin LL-37 in Gastrointentinal Cells," Molecular Immunology, 41(9): 847-854.

Schwab, Markus, et al. (2007) "Role of Nuclear Hormone Receptors in Butyrate-Mediated Up-Regulation of the Antimicrobial Peptide Cathelicidin in Epithelial Colorectal Cells," Molecular Immunology, 44(8): 2107-2114.

Sherwin, C.P., "Acetylation as a Physiologic Reaction," Scientific Proceedings (1924), 22, 182.

Tanaka, T., et al., "Ligands for Peroxisome Proliferator-Activated Receptors α and γ Inhibit Chemically Induced Colitis and Formation of Aberrant Crypt Foci in Rats," Cancer Res., 61: 2424-2428 (2001).

Tuleu, et al., "Colonic delivery of 4-aminosalicylic acid using amylose-ethyl cellulose-coated hydroxypropyl methyl cellulose capsules," Aliment Pharmacol Ther., (2002); 167: 1771-1779.

van't Riet, Bart, et al. (1979) "Synthesis of Hydroxy and Amino-Substituted Benzohydroxamic Acids: Inhibition of Ribonucleotide Reductase and Antitumor Activity," Journal of Medicinal Chemistry, 22(5): 589-592.

Wang, R., et al., "Further Development and Validation of Emphirical Scoring Functions for Structure-Based Binding Affinity Prediction," J. Comput. Aided Mol. Des., 16: 11-26 (2002).

Wang, Tian-Tian, et al. (2004) "Cutting Edge: 1,25-Dihydroxyvitamin D3 is a Direct Inducer of Antimicrobial Peptide Gene Expression," The Journal of Immunology, 173: 2909-2912.

Westin, S., et al., "Interactions Controlling the Assembly of Nuclear-Receptor Heterodimers and Co-Activators," Nature, 395: 199-202 (Sep. 1998).

Williams, J.G., et al. (1989) "Effect of Sulphasalazine and its Active Metabolite, 5-Amino-Salicylic Acid, on Toxic Oxyden Metabolite Production by Neutrophils," Gut, 30: 1581-1587.

Written Opinion of the International Searching Authority for PCT/IE2006/000076 mailed Feb. 1, 2007.

Xu, H.E., et al., "Structural Determinants of Ligand Binding Selectivity Between the Peroxisome Proliferator-Activated Receptors," Proc. Natl. Acad. Sci. U.S.A., 98: 13919-13924 (2001).

Yanai, K., et al., "Para-Position Derivatives of Fungal Anthelmintic Cyclodepsipeptides Engineered with Streptomyces Venezuelae Antibiotic Biosynthetic Genes," Nature Biotechnology (2004) 22, 848-855.

Youssef, J., et al., "Role of Peroxisome Proliferator-Activated Receptors in Inflammation Control," J. Biomed Biotechnol. 3: 156-166 (2004).

* cited by examiner

FIGURE 1

|  | concentration (mM) | | | |
| --- | --- | --- | --- | --- |
| Compound | 0.75 | 1.5 | 3 | 10 |
| 5-ASA | 2 | 5 | 14 | 40 |
| 2-14 | 18 | 51 | 80 | 97 |
| 2-20 | 0 | 0 | 0 | 14 |
| 2-26 | 2 | 12 | 50 | 69 |
| 2-31 | 0 | 0 | 0 | 0 |
| 2-38 | 11 | 19 | 23 | 51 |
| 2-39 | 0 | 0 | 0 | 6 |

A

B

A

B

Ctr

14

CTR 14

LIVER

LUNG

METHODS FOR PREVENTING OR REDUCING COLON CARCINOGENESIS

RELATED APPLICATIONS

This application is a national stage filing under 35 U.S.C. §371 of PCT/EP2009/008633, filed Dec. 3, 2009, which claims priority to EP08425775.7, filed Dec. 5, 2008; U.S. Ser. No. 61/157,674, filed Mar. 5, 2009; and U.S. Ser. No. 61/222,281 filed Jul. 1, 2009, all of which are hereby incorporated by reference.

BACKGROUND

Colorectal cancer is a serious complication in patients with ulcerative colitis or Crohn's disease. Early age at diagnosis, the extent and severity of colonic disease, the presence of primary sclerosing cholangitis, and/or a family history of cancer represent independent risk factors for the development of colorectal cancer. Aspirin has been found to exert chemopreventive effects in colon cancer, but the mechanism by which it exerts these effects is complex.

One target for activity of chemopreventive drugs against cancers such as colorectal cancer and solid tumor cancers and adenocarcinomas (such as breast, prostate, lung and heptocellular carcinoma) may be improvement of DNA replication. The fidelity of DNA replication is a product of polymerase accuracy, its proofreading activity, and/or the proficiency of the postreplicational mismatch repair system. Inefficiency of fidelity replication can be a key to the development of human cancer. Chemopreventive drugs that increase such efficiency in colorectal cells could significantly reduce the life-threatening manifestations of cancer and diminish cancer deaths. However, some drugs that may have chemopreventive potential, such as 5-amino salicyclic acid, are inactivated and eliminated from circulation when give systemically; 5-amino-salicyclic acid, when orally administered, does not reach the left colon, where may sporadic and colitis-related colorectal cancers develop.

There remains a need for chemopreventative drugs that, for example, when given orally, remain activated for an amount of time so that such drugs may reach affected areas of the body, or areas of the body at risk for cancer, e.g. the left colon.

SUMMARY

This disclosure is directed in part to methods of preventing and/or reducing colon, solid tumor, and/or adenocarcinoma carcinogenesis, e.g. minimizing or prolonging a manifestation of colon cancer comprising administering compounds disclosed herein to a patient, e.g. a human.

For example, a method of preventing or reducing colon carcinogenesis or other carcinogenesis (e.g., adenocarcinoma) is provided, comprising: administering to a patient at risk of cancer e.g. at risk of colon cancer, a pharmaceutical preparation comprising a chemopreventive agent represented by:

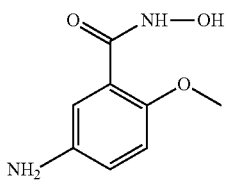

or pharmaceutically acceptable salts and/or stereoisomers thereof.

For example, methods disclosed herein may include methods wherein the patient is human. A patient may or may not have, for example, detectable colorectal cancer. In some embodiments, upon or before administration, spontaneous mutation frequency of a colon carcinoma cells are present in the patient. In other embodiments, the patient has Crohn's disease, inflammatory bowel disease, or ulcerative colitis.

Also provided herein are methods for delaying clinical manifestation of a colorectal tumor (or, e.g., a solid tumor or adenocarcinomas, e.g. lung, breast, pancreas, prostate or hepatocellular carcinoma) in a patient at risk of cancer, e.g., colon cancer, comprising administering to the patient an effective amount of a chemopreventive compound as described above. For example, the delay is at least 1 year as compared to a patient who is not administered a chemopreventive compound. In another embodiment, a patient may have at least about a 30% reduction of the mutation rate of carcinoma cells, e.g. colon carcinoma cells, present in the patient.

These and other aspects and advantages of the invention will become apparent upon consideration of the following figures, detailed description, and claims.

BRIEF DESCRIPTION OF THE DRAWINGS

The invention can be more completely understood with reference to the following drawings.

FIG. 1 indicates percentage of growth inhibition, assessed by flow cytometry of CFSE-labeled HCT 116 cells, following treatment with increasing doses of 5-ASA and compounds 14, 20, 26, 31, 38, 39 as disclosed herein.

DETAILED DESCRIPTION

Figure 2:
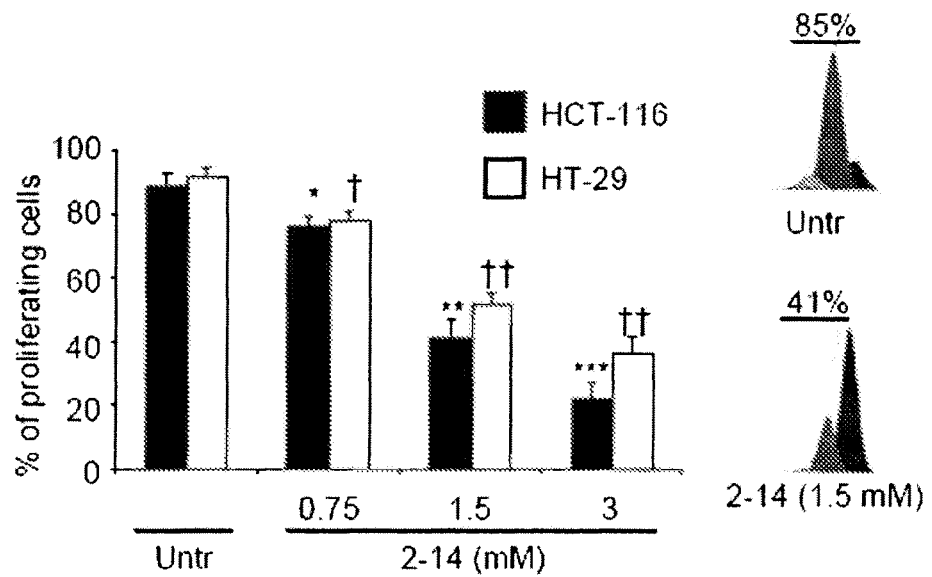
FIG. 2 depicts inhibition the growth of HCT-116 and HT-29 cells with compound 14; CFSE-labeled cells were left untreated (Untr) or treated with compound 14 (referred to as 2-14 in some Figures).

The invention is based, in part, upon the discovery that certain compounds disclosed herein have the ability to improve the replication fidelity in cancer cells, for example, in colorectal cancer cells. In one aspect, the disclosure is directed to methods of preventing or reducing the incidence of cancer, e.g. colon cancer, in, for example, patients at risk of and/or having risk factors indicating a susceptibility of developing cancers such as colon cancers. The disclosed methods comprise administering a compound disclosed herein to a patient in need thereof.

Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

A "patient," "subject" or "host" to be treated by the subject method may mean either a human or non-human animal, e.g. a small mammal such as a mouse or rat, and including horse, cow, dog, cat, etc.

The term "therapeutic agent" is art-recognized and refers to any chemical moiety that is a biologically, physiologically, or pharmacologically active substance that acts locally and/or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment.

The term "therapeutic effect" is art-recognized and refers to a local and/or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art. For example, certain compositions of the present invention may be administered in a sufficient amount to produce a at a reasonable benefit/risk ratio applicable to such treatment.

The term "treating" is art-recognized and refers to curing as well as ameliorating at least one symptom of any condition or disease.

The term "alkyl" is art-recognized, and includes saturated aliphatic groups, including straight-chain alkyl groups, branched-chain alkyl groups, cycloalkyl(alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer, e.g. from 1 to 6 carbons. Likewise, cycloalkyls have from about 3 to about 10 carbon atoms in their ring structure, and alternatively about 5, 6 or 7 carbons in the ring structure. The term "alkyl" is also defined to include halosubstituted alkyls.

Moreover, the term "alkyl" (or "lower alkyl") includes "substituted alkyls", which refers to alkyl moieties having substituents replacing a hydrogen on one or more carbons of the hydrocarbon backbone. Such substituents may include, for example, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN and the like. Exemplary substituted alkyls are described below. Cycloalkyls may be further substituted with alkyls, alkenyls, alkoxys, alkylthios, aminoalkyls, carbonyl-substituted alkyls, —CN, and the like.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The definition of each expression, e.g. alkyl, m, n, and the like, when it occurs more than once in any structure, is intended to be independent of its definition elsewhere in the same structure.

Certain compounds contained in compositions of the present invention may exist in particular geometric or stereoisomeric forms. In addition, compounds of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and non-aromatic organic compounds that may be substituted or unsubstituted.

The term "pharmaceutically-acceptable salts" is art-recognized and refers to the relatively non-toxic, inorganic and organic acid addition salts of compounds, including, for example, those contained in compositions of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Compounds

Compounds contemplated for use in the disclosed methods include compounds represented by formula I, or a pharmaceutically acceptable salt, enantiomer or stereoisomer thereof:

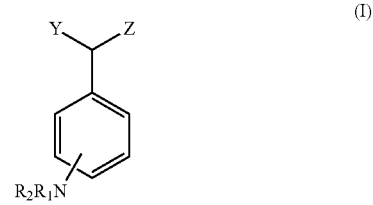

(I)

wherein:

$R_1$ and $R_2$, are each independently selected from the group consisting of H and $C_{1-6}$ alkyl; or $R_1$ and $R_2$ together with the nitrogen atom they are bonded to form an aromatic or aliphatic ring with 5 or 6 atoms which may be optionally substituted;

Y and Z are each independently selected from the group consisting of H, OH, COOH, —$OR_3$, —$CH(OR_3)COOH$; and $R_3$ is selected from the group consisting of H, phenyl, benzyl, vinyl, allyl, $C_{1-6}$ alkyl or $C_{1-6}$ alkyl substituted by one or more halogens.

In an embodiment, Y may be H or COOH. For example, Y may be H and Z may be $CH(OR_3)COOH$, or Y may be COOH and Z maybe —$OR_3$. In some embodiments, $R_3$ may be methyl, ethyl, n-propyl, or isopropyl.

In other embodiments, the $NR_1R_2$ moiety may be in the 4' position or may be in the 3' position. In certain embodiments, $R_1$ and $R_2$ are H.

Exemplary compounds also include those represented by formulas IIa or IIb or a pharmaceutically acceptable salt, enantiomer or stereoisomer of:

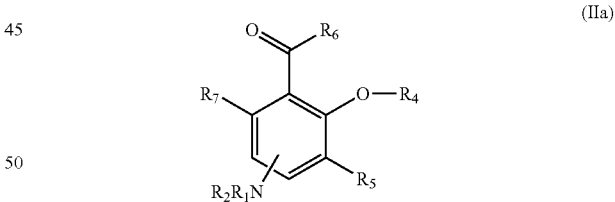

(IIa)

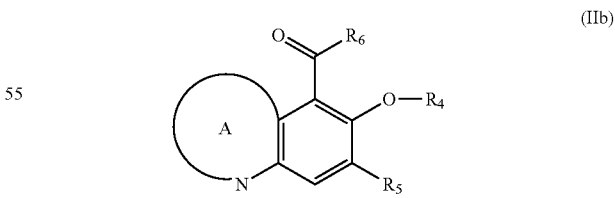

(IIb)

wherein:

$R_1$ and $R_2$ are each independently selected from the group consisting of H and $C_{1-6}$ alkyl; or $R_1$ and $R_2$ together, with the nitrogen atom they are bonded to, form an aromatic or aliphatic ring with 5 or 6 atoms;

$R_6$ is selected from the group consisting of: —NHOH, OH, and —$OR_9$;

$R_9$ is $C_{1-6}$ alkyl;

$R_4$ is selected from H, phenyl, benzyl, vinyl, allyl, $C_{1-6}$ alkyl or $C_{1-6}$ alkyl substituted by one or more halogens;

$R_5$ and $R_7$ are each independently hydrogen or halo, or; or $R_4$ and $R_5$, or $R_4$ and $R_6$ together, form a fused heterocyclic ring with 5 or 6 atoms, optionally substituted with halo or $C_{1-6}$ alkyl; and A is a fused heterocyclic ring; or a pharmaceutically acceptable salt thereof.

In certain embodiments, the $NR_1R_2$ moiety of formula IIa may be in the 4' position or may be in the 3' position. In certain embodiments, $R_1$ and $R_2$ are H.

$R_9$, in some embodiments, may be methyl, ethyl, n-propyl, or isopropyl.

In some embodiments a compound can be represented by

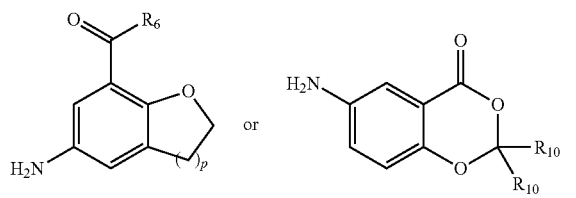

wherein p is 1 or 2, $R_6$ is OH or $-OR_9$, wherein R9 is defined above, and $R_{10}$, independently for each occurrence, is selected from the group consisting of H, halo, or $C_{1-6}$ alkyl, e.g. methyl or ethyl.

Exemplary compounds contemplated herein include:

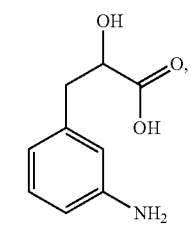
(II)

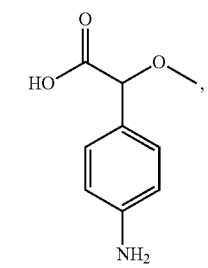
(III)

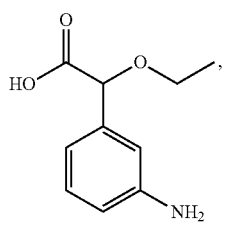
(IV)

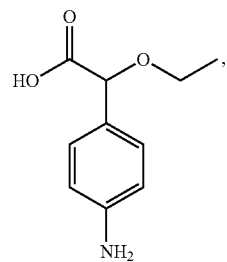
(V)

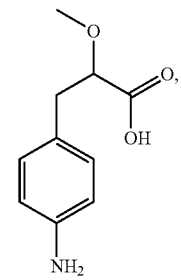
(VI)

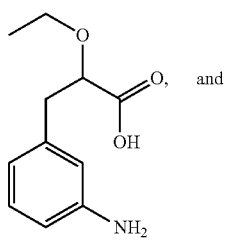
(VIII)

and

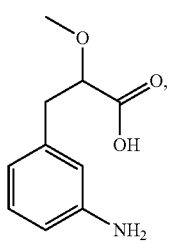
(IX)

or a pharmaceutically acceptable salt thereof.

In some embodiments, contemplated compounds include: 4-amino-N-hydroxy-2-methoxybenzamide (compound 13); 6-methoxy quinoline-5-carboxylic acid (compound 36); 6-methoxy-1,2,3,4-tetrahydroquinoline-5-carboxylic acid (compound 37); 5-diisopropylaminosalicylic acid (compound 38).

Other exemplary compounds include those represented by:

(compound 13):

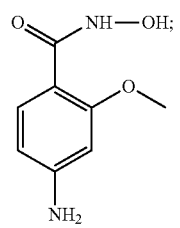

-continued (compound 14):

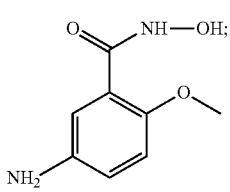

(compound 26):

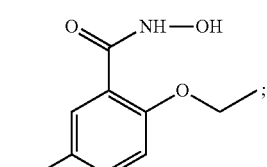

(compound 17):

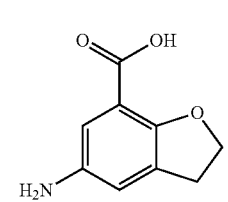

(compound 31):

(compound 28):

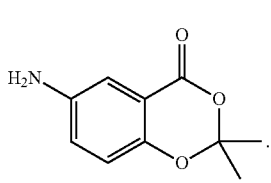

Compounds contemplated herein include racemic mixtures, and enantiomers of compounds, for example: (±)-2-hydroxy-3-(3'-aminophenyl) propionic acid (compound 20); (±)-2-methoxy-2-(4'-aminophenyl) acetic acid (compound 23); (±)-2-ethoxy-2-(3'-aminophenyl) acetic acid (compound 32); (+)-2-ethoxy-2-(4'-aminophenyl) acetic acid (compound 33); (±)-2-methoxy-3-(4'-aminophenyl) propionic acid (compound 34) "±34" (racemic form); (±)-2-ethoxy-3-(4'-aminophenyl) propionic acid (compound 39); (±)-2-ethoxy-3-(3'-aminophenyl) propionic acid (compound 40).

For example, the compounds used in the methods of the present invention can be enantiomers of the following racemic mixtures: (R,S)-2-hydroxy-2-(3-aminophenyl)acetic acid (compound 10); (R,S)-2-hydroxy-2-(4-aminophenyl) acetic acid (compound 11); (R,S)-2-hydroxy-3-(4'-aminophenyl)propionic acid (compound 21); (R,S)-2-methoxy-2-(3'-aminophenyl)acetic acid (compound 22); (R,S)-2-methoxy-3-(3'-aminophenyl)propionic acid (compound 35); (R,S)-2-methoxy-3-(4-aminophenyl)propionic acid (compound 34), as well as enantiomers, e.g.: (+) 2-S-methoxy-3-(4-aminophenyl)propionic acid (compound 34); (−) 2-R-methoxy-3-(4-aminophenyl)propionic acid (compound 34).

Other racemic type mixtures of compounds contemplated include: e.g. (±)-2-hydroxy-2-(3'-aminophenyl)acetic acid (compound 10); (±)-2-hydroxy-2-(4'-aminophenyl)acetic acid (compound 11); (±)-2-hydroxy-3-(4'-aminophenyl)propionic acid (compound 21) and (±)-2-methoxy-2-(3'-aminophenyl)acetic acid (compound 22).

Further compounds contemplated for use in the disclosed methods: 5-aminosalicylo-hydroxamic acid (compound 5); 3-dimethylaminosalicylic acid (compound 6); 2-methoxy-4-aminobenzoic acid (compound 7); 2-methoxy-5-aminobenzoic acid (compound 8); 5-methylaminosalicylic acid (compound 9); 4-methylaminosalicylic acid (compound 12); 4-acetylaminosalicylic acid (compound 16); 2-ethoxy-4-aminobenzoic acid (compound 18); 2-ethoxy-5-aminobenzoic acid (compound 19); 4-dimethylaminosalicylic acid (compound 24); 2-ethoxy-4-aminobenzoylhydroxamic acid (compound 25); 6-hydroxyquinoline-5-carboxylic acid (compound 27); 2-(2-propyl)oxy-4-aminobenzoic acid (compound 30); 4-(1-piperazinyl)salicylic acid (compound 41); (R,S) 5-oxa-quinoline-6-carboxylic acid (compound 15); 6-methoxy quinoline-5-carboxylic acid (compound 36); 6-methoxy-1,2,3,4-tetrahydroquinoline-5-carboxylic acid (compound 37); 5-diisopropylaminosalicylic acid (compound 38); and 4-diisopropylaminosalicylic acid (compound 42).

Methods for making contemplated compounds may be found for example in WO2007/010516 and WO2007/010514, each hereby incorporated by reference in their entirety.

Therapeutic Applications

Methods of preventing or reducing colon carcinogenesis or colon cancer form part of this disclosure. Such methods may comprise administering to a patient, for example, a patient at risk of colorectal cancer, a pharmaceutical preparation comprising a chemopreventive agent such as those disclosed herein, e.g., formula I, IIa, IIb, and compounds disclosed herein. A patient at risk of colon cancer or colon carcinogenesis may include those patients with ulcerative colitis, inflammatory bowel disease, or Crohn's disease. A patient at risk may also include those patients with an early age at diagnosis of Crohn's or colitis, extensive and/or severe of colonic disease, patients with the presence of primary sclerosing cholangitis, and/or patients having a family history of cancer. Patients at risk of colorectal cancer can include those patients with a family history of such cancer (for example patients with familial adenomatous polyposis or hereditary nonpolyposis) and/or patients having chronic ulcerative colitis, and/or polyps such as adenomatous polyps.

Patients treated using the above method may or may not have detectable colorectal cancer. In an different embodiment, spontaneous mutation frequency of a colon carcinoma cells may or may not be present in the patient before initial administration, or during the administration of a course, of a compound disclosed herein. In some embodiments, the patient has at least about a 5%, 10%, 20%, 30%, 40% or even 50% or more reduction of the mutation rate of colon carcinoma cells present in the patient after administering a disclosed compound, after e.g. 1 day, 2 days, 1 week, 1 month or 6 months or more. Without being bound by any theory, compounds disclosed herein may reduce mutation rate by interacting with cellular machineries involved in progression through the cell cycle. Such a progression may result in slowing down processes such as DNA replication (S phase) and/or cell division (mitosis) through the onset of cell cycle checkpoints, which would give the cell the opportunity to either repair the damage that the DNA may have encountered or undergo apoptosis. In both cases, this would prevent accumulation of mutated or damaged cells and would lead to maintenance of DNA integrity.

Also contemplated herein is a method for delaying clinical manifestation of a colorectal tumor, or a solid tumor (e.g., a breast, prostate, lung or hepatocellular carcinoma) in a patient, for example, a patient at risk of cancer e.g. colon cancer, comprising administering to the patient an effective amount of a chemopreventive compound disclosed herein, e.g. a formula I, IIa or IIb. Patients at risk of contemplated cancers include those genetically disposed as compared to the general population, of e.g. having breast cancer, or those patients who have or currently are tobacco users (e.g. at a higher risk of lung cancer as compared to non-tobacco users).

Administering such a compound may be on e.g., at least a daily basis. The delay of clinical manifestation of a tumor, e.g. a colorectal tumor, in a patient as a consequence of administering a compound disclosed here may be at least e.g., 6 months, 1 year, 18 months or even 2 years or more as compared to a patient who is not administered a chemopreventive compound such as one disclosed herein. Such methods include administering systemically (e.g. orally) to a patient an effective amount of a disclosed compound.

For example, provided herein are compositions that may be suitable for systemic administration to a patient having a colorectal tumor, said composition comprising a compound represented by formula I, IIa or IIb and a pharmaceutically acceptable excipient or carrier; wherein the compound is present in an amount effective to inhibit the growth of the tumor when administered systemically. Such inhibition of tumor growth may be, for example, measured as a delay in tumor doubling time. Compositions may, in some embodiments, extend the tumor doubling time by a factor of two, three, four or even 5 or 10. In another embodiment, growth of a tumor may be measured by a reduction in the volume of said tumor, and a disclosed composition may, when administered to a patient, e.g., a mammal, result in reduction of the volume of the tumor by at least 10%, 20%, 30%, 50%, 70%, 80% or more.

In an embodiment, a compound represented by formula I, IIa, or IIb may be more effective, for example, more than about two, three, five or even ten times more effective than 5-amino salicylic acid (mesalazine), for preventing or reducing colon carcinogenesis in a patient in need thereof.

Also forming part of this disclosure are methods of preventing or reducing solid tumors or adenocarcinomas, such as breast, cervix, pancreas, prostate adenocarcinomas and/or hepatocellular carcinomas. Such methods may comprise administering to a patient, for example, a patient at risk of such cancers, a pharmaceutical preparation comprising a chemopreventive agent such as those disclosed herein, e.g., formula I, IIa, IIb, and compounds disclosed herein.

Generally, a therapeutically effective amount of active component will be in the range of from about 0.1 mg/kg to about 100 mg/kg, optionally from about 1 mg/kg to about 100 mg/kg, optionally from about 1 mg/kg to 10 mg/kg. The amount administered will depend on variables such as the type and extent of disease or indication to be treated, the overall health status of the particular patient, the relative biological efficacy of the binding protein delivered, the formulation of the binding protein, the presence and types of excipients in the formulation, and the route of administration. The initial dosage administered may be increased beyond the upper level in order to rapidly achieve the desired blood-level or tissue level, or the initial dosage may be smaller than the optimum and the daily dosage may be progressively increased during the course of treatment depending on the particular situation. Human dosage can be optimized, e.g., in a conventional Phase I dose escalation study designed to run from 0.5 mg/kg to 20 mg/kg. Dosing frequency can vary, depending on factors such as route of administration, dosage amount and the disease condition being treated. Exemplary dosing frequencies are once per day, once per week and once every two weeks.

Contemplated formulations or compositions comprise a disclosed compound and typically include a compound a pharmaceutically acceptable carrier.

Compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent. In some embodiments, compositions and methods disclosed herein include systemic administration, which includes for example, intraperitoneal administration. In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, film-coated tablets, sugar-coated tablets, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3)

humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

Formulations and compositions may include micronized crystals of the disclosed compounds. Micronization may be performed on crystals of the compounds alone, or on a mixture of crystals and a part or whole of pharmaceutical excipients or carriers. Mean particle size of micronized crystals of a disclosed compound may be for example about 5 to about 200 microns, or about 10 to about 110 microns.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as film coated tablets or sugar coated tablets, capsules, pills and granules, may optionally be scored or prepared with coatings and shells, such as enteric coatings and other coatings well known in the pharmaceutical-formulating art.

Liquid dosage fauns for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal or topical administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants. The efficacy of treatment with the subject compositions may be determined in a number of fashions known to those of skill in the art.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Except where indicated otherwise, the order of steps or order for performing certain actions are immaterial so long as the invention remains operable. Moreover, unless otherwise noted, two or more steps or actions may be conducted simultaneously.

EXAMPLES

Example 1

Cell Proliferation-Colorectal

All reagents used in Examples 1-3 were from Sigma-Aldrich (Milan, Italy) unless specified. Compounds were dissolved as a 25 mM stock solution in culture medium, and the pH of the solution was adjusted to 7.4, if necessary, with NaOH. The human CRC cell lines, HCT-116 and HT-29 (expressing either wild-type or mutated p53 respectively), were maintained in McCoy's 5A supplemented with 10% fetal bovine serum (FBS), 1% penicillin/streptomycin, and 50 µg/ml gentamycin. The murine CRC cell line, CT26, was maintained in RPMI 1640 medium supplemented with 10% FBS and 1% penicillin/streptomycin.

Cell Proliferation

For cell growth assays, serum-starved HCT-116, HT-29, and CT26 cells were plated in appropriate complete medium at $2\times10^5$ cells/ml/well in 6-well culture dishes and allowed to adhere overnight. Cells were then labeled with carboxyfluorescein diacetate succinimidyl ester (CFSE) (Invitrogen, Milan Italy) at 37° C. according to the manufacturer's instruction. After 30 minutes, the medium was removed and fresh media containing 0.05% bovine serum albumin (BSA), and increasing doses of 5-ASA or disclosed compounds were added. After 24 hours, cells were collected, washed twice with PBS 1x, and then incubated with 5 µg/ml of PI for 15 minutes, at 4° C. in the dark. CFSE and/or PI-positive cells were determined by flow cytometry (Becton Dickinson, FACSCalibur, Milan, Italy). To determine whether the negative effect of compound 14 (2-methoxy-5-amino-N-hydroxybenzamide) on proliferation was reversible, cells were cultured in the presence or absence of compound 14 (1.5 and 3 mM) for 24 hours (1st culture). Afterwards, cells were either left untreated or extensively washed and cultured with medium in the absence of compound 14 for additional 24 hours (2nd culture). The percentage of proliferating cells was then evaluated by flow cytometry.

FIG. 1 shows that compound 14 has a pronounced antiproliferative effect and is about ten times more potent than 5-ASA in inhibiting CRC (colorectal cancer) cell proliferation.

FIG. 2 confirms that compound 14 dose-dependently inhibited the proliferation of both HCT-116 and HT-29 cells. Data indicate mean±SD of 4 experiments (HCT-116: untreated vs compound 14-treated cells, * P=0.02,  P=0.005, * P<0.001; HT-29: untreated vs compound 14-treated cells, †P=0.006, ††P<0.001). Right insets of FIG. 2 are representative histograms of HCT-116 cells left untreated or treated with compound 14. Numbers above lines indicate the percentages of proliferating cells.

Figure 3:
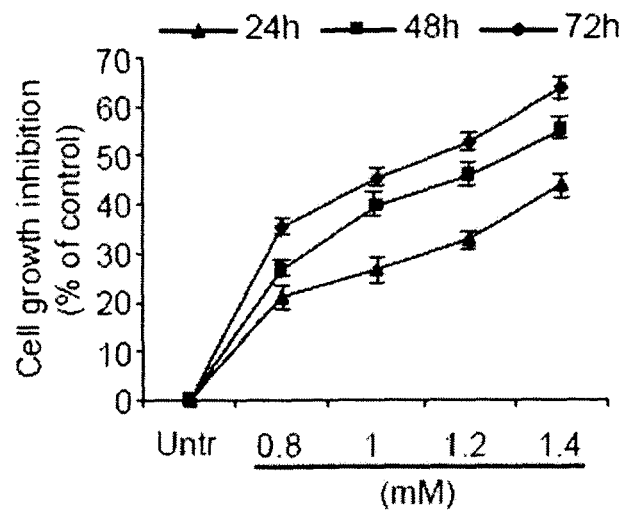
FIG. 3A depicts inhibition of HCT-116 cell growth in a time-dependent manner.
FIG. 3B depicts reversible inhibition.
Figure 3:
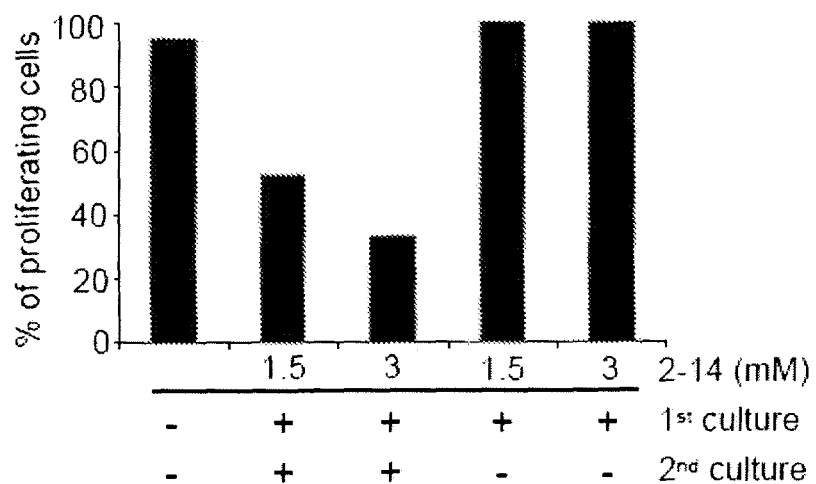

The anti-proliferative effect of compound 14 was time-dependent (FIG. 3A). HCT-116 cells were either left untreated or treated with increasing doses of compound 14 for 24, 48, and 72 hours respectively. Data indicate mean±SD of 3 experiments.

Figure 4:
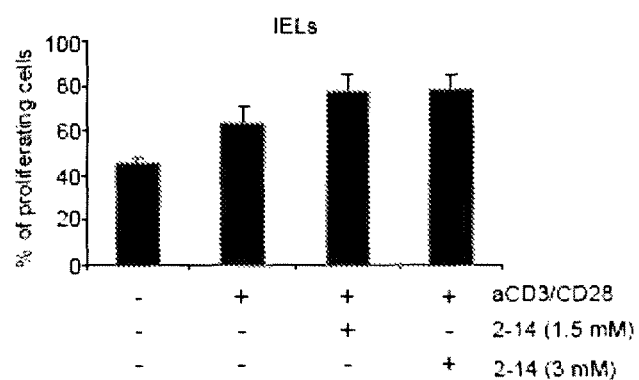
FIG. 4A shows representative histograms showing the percentage of proliferating colonic IEL (intra-epithelial lymphocytes) either left untreated or treated with anti-CD3/CD28 in presence or absence of graded doses of compound 14 for 48 hours; Data indicate mean±SD of 3 experiments.
FIG. 4B are histograms showing the percentage of proliferating fibroblasts either left untreated or treated with compound 14 for 48 hours; Data indicate mean±SD of 3 experiments.
Figure 4:
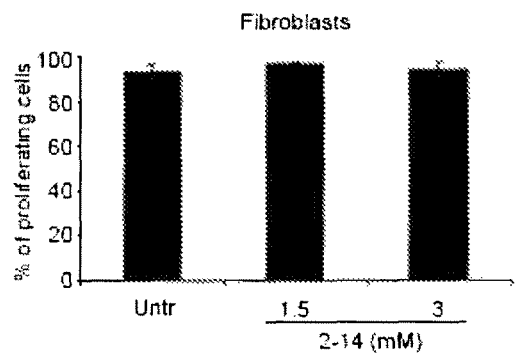

The effect was fully reversible, as CRC cells proliferated regularly upon removal of the compound (FIG. 3B). Representative histograms showing the percentage of proliferating HCT-116 cells cultured in the presence or absence of compound 14 (1.5-3 mM) for 24 hours (1st culture). Afterwards, cells were either left untreated or extensively washed and cultured with medium in the absence of compound 14 for additional 24 hours (2nd culture). One of 3 separate experiments is shown. No effect was observed in cells treated with equivalent concentrations of mannitol clearly indicating that the effect of compound 14 is not due to osmotic shifts in the culture medium (data not shown). Compound 14 did not affect the proliferation of normal colonic intra-epithelial lymphocytes and fibroblasts (FIG. 4).

Cell Cycle

Figure 5:
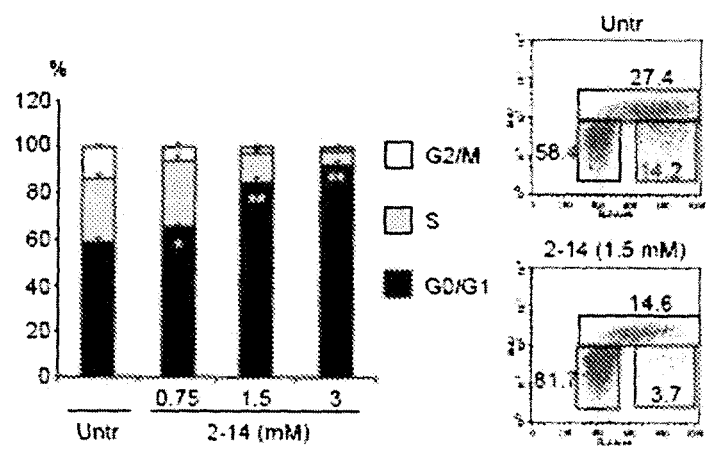
FIG. 5 shows that compound 14 treated cells accumulate in G0/G1 phase.

For analysis of cell cycle distribution, serum-starved cells were cultured in medium containing 0.05% BSA and the desiderated concentrations of compound 14 for 24 hours. Cells were pulsed with 10 µM BrdU for 60 minutes, then collected, washed twice with PBS 1x, fixed in 70% cold ethanol, and stored at −20° C. for at least 3 hours. Afterwards, cells were washed twice with PBS 1x, denatured in 2M HCl and stained with anti-BrdU monoclonal antibody (Immunotech, Marseille, France) followed by FITC-conjugated secondary anti-mouse IgG (Molecular Probes/Invitrogen, Milan, Italy). After staining with 100 µg/ml PI, cells were analyzed by flow cytometry. Increasing concentrations of the compound caused a progressive accumulation in the numbers of cells in G0/G1 phase and a decrease of cells with S and G2/M phase DNA content. HCT-116 cells were treated with or without compound 14 for 24 hours. Values in FIG. 5 are the percentages of cells in the different phases of cell cycle and indicate mean±SD of 4 experiments (untreated vs compound 14-treated cells * P<0.04, ** P<0.001). Right insets show representative dot-plots of the cell cycle distribution.

Figure 6:
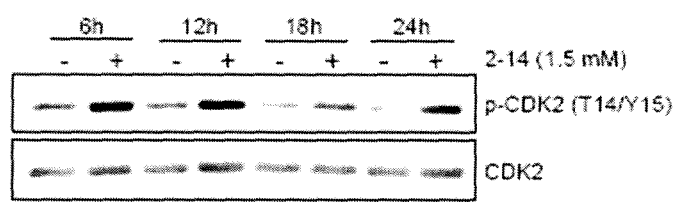
FIG. 6 indicated the effect of compound 14 on CDK2 phosphorylation at Thr-14 and Tyr-15 residues.

Compound 14 treated HCT-116 cells, treated with or without compound 14 for the indicated time points in FIG. 6, also exhibited inactivation of CDK2, marked by enhanced phosphorylation of this kinase on threonin 14 and tyrosine 15 residues as shown in FIG. 6. p-CDK2 and total CDK2 were analyzed by Western blotting. One of 4 representative Western blots is shown.

Example 2

In-Vivo Formation of CT26-Derived Tumors

CT26 cells ($1\times10^5$ cells in 300 µl PBS 1x) were injected subcutaneously into the flank of Balb/c mice, whose fur was shaved and depilated. Five groups of 10 mice each were implanted with CT26. The first group received daily subcutaneously 300 µl PBS (control), the remaining groups received daily subcutaneously compound 14 at a final dose of 1, 4, 8, or 12 mg/kg/mouse dissolved in 300 µl PBS. Both compound 14 and PBS were administered starting on day 3. Further experimentation was performed to assess whether compound 14 had anti-cancer activity when administered systemically. To this end, 3 days after the CT26 inoculation, mice were injected with PBS or compound 14 (8 mg/kg/mouse) intraperitoneally. As a control, mice received subcutaneously compound 14 (8 mg/kg/mouse). Mice were monitored over the time for weight loss. After 2 weeks, mice were sacrificed, tumors were photographed, then excised and their mass calculated according to the following formula: ½× (short diameter)×(long diameter)×(height). Total extracts were prepared from xenografts and analyzed for cyclin D1 protein content by Western blotting using a commercially available antibody (Santa Cruz Biotechnology). To examine whether compound 14 was able to reduce the growth of established CRC xenografts, Balb/c mice were implanted with CT26 as described above. After 2 weeks, mice with similar tumor size, determined by caliper measurements, were divided into three groups of 8 mice each. The first group received daily subcutaneously 300 µl PBS (control), the second group received daily subcutaneously 5-ASA (80 mg/kg) dissolved in 300 µl PBS. The last group received daily subcutaneously compound 14 (8 mg/kg) dissolved in 300 µl PBS. Mice were monitored over the time for weight loss. After 2 weeks, mice were sacrificed, tumors were photographed, then excised and their mass calculated as described above. Studies were approved by the Local Ethical Committee.

No body weight loss was observed during the study in both control and treated groups, and all animals survived until the end of study. Fourteen days after injection, CT26-derived macroscopic tumors were evident in 10/10 control mice, 5/10 mice treated with subcutaneously compound 14, and 7/10 mice treated with intraperitoneally compound 14. Mice treated with compound 14 exhibited a significant decrease in the tumor mass in comparison to controls; the anti-neoplastic effect of compound 14 was dose-dependent, and it was seen regardless of whether the drug was given subcutaneously or intraperitoneally, underlying the difference between 5-ASA because 5-ASA is not effective in controlling CRC growth if administered systemically.

Figure 7:
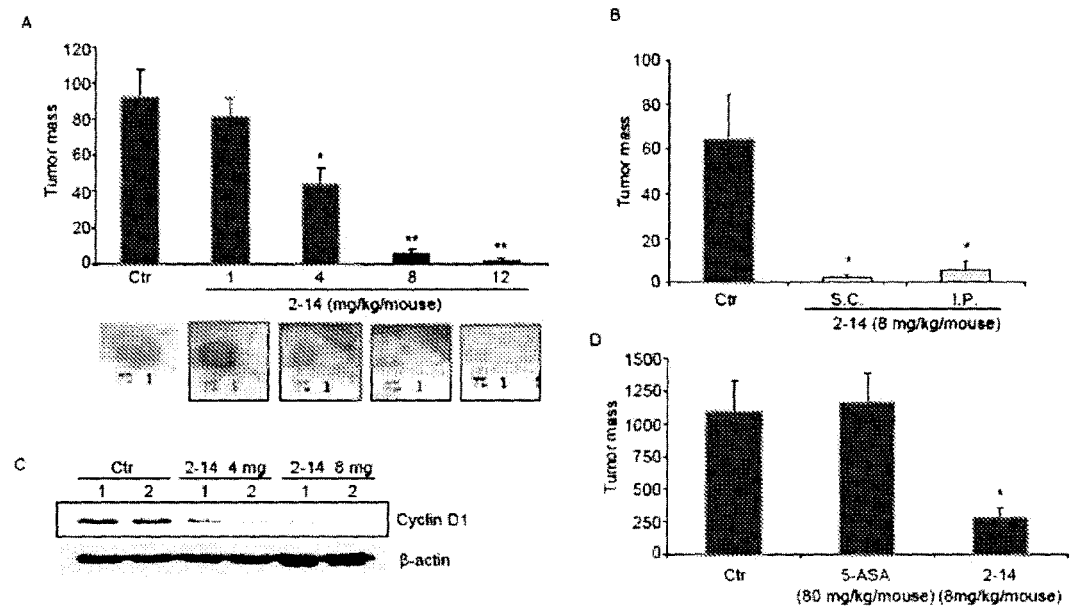
FIGS. 7A and B shows administration of compound 14 dose-dependently reduces the in vivo formation of CT26-derived tumors in mice.
FIG. 7C shows the results of subcutaneous injection of mice with compound 14 on cyclin D1 protein expression.
FIG. 7D depicts results of subcutaneous injection of mice with compound 14 on size of stabilized CT26 derived tumors.

FIG. 7A shows that administration of compound 14 dose-dependently reduces the in-vivo formation of CT26-derived tumors. Representative photographic images of CT26 xenografts developed in control (ctr) and in compound 14-treated mice are shown at the bottom of the respective histograms (control vs. compound 14-treated mice, *P<0.01; ** P<0.001). FIG. 7B indicates that compound 14 inhibits CT26-derived xenografts when administered intra-peritoneally. Control mice received daily PBS. Data indicate mean±SD of all experiments (control vs compound 14-treated mice * P<0.001).

Western blotting of proteins prepared from xenografts showed that compound 14 reduced cyclin D1 protein expression (FIG. 7C). Cyclin D1 protein expression in total extracts of CT26-derived tumors treated with PBS (Ctr) or with two different doses of compound 14. One of 3 separate experiments in which similar results were obtained is shown. Histological analysis of liver, kidney, spleen, and colon revealed no morphological alteration in mice receiving compound 14.

To examine whether compound 14 reduces the growth of established CRC xenografts, CT26-derived tumors were induced as above, and at day 14, mice were randomly allocated into 3 groups and injected subcutaneously with compound 14 (8 mg/kg mouse/day), 5-ASA (80 mg/kg mouse/day) or vehicle (PBS) for 2 weeks. Mice were monitored over the time and sacrificed at day 28. Compound 14 but not 5-ASA significantly reduced the tumor size as compared to mice treated with PBS. FIG. 7D indicates that subcutaneous administration of compound 14 reduces the size of stabilized CT26-derived tumors. Data indicate mean±SD of all experiments (control vs compound 14-treated mice * P=0.003).

Example 3

Induction of Colitis-Associated Colon Cancer

Balb/c mice were given a first i.p. injection of AOM (10 mg/kg) on day O, Seven days after the AOM injection, the mice were given 2% DSS in the drinking water for 7 days. One week after the discontinuation of DSS administration, the mice were given a second i.p. injection of AOM (5 mg/kg). Then, 7 days after the second AOM injection, the mice were again given 2% DSS in the drinking water for 7 days. Two weeks later, the mice were randomly divided into two groups receiving i.p. injection of PBS or 16 mg/kg/mouse compound 14 every second day, for 49 days until sacrifice. (To rule out the possibility that compound 14 could interfere with the ongoing mucosal inflammation, treatment was started 2 weeks after the last DSS administration.) Mice were endoscopically screened, and neoplastic lesions were scored as previously described All mice were sacrificed at the end of the study, and colonic samples were used for histological analysis and isolating lamina propria mononuclear cells (LPMC). An aliquot of LPMC was assessed for the expression of CD4, CD8, and CD25 by flow-cytometry using the following antibodies (CD4: cat. 552051, BD Pharmigen, Milan, Italy; CD8: cat. 22150084S and CD25: cat. 22150253, Immunotools, Friesoythe, Germany), while the remaining LPMC were used for extracting RNA and assessing the expression of COX-2, TNFα, and IL-1β by real-time PCR. To this end, the following primers were used: COX-2: FWD: 5'-TTCTTTGC-CCAGCACTTCAC-3'; REV: 5'-GGATACACCTCTCCAC-CAAT-3', TNFα: FWD: 5'-ACCCTCACACTCAGATCATC-3'; REV: 5'-GAGTAGACAAGGTACAACCC-3, IL-1β: FWD: 5'-TCAGGCAGGCAGTATCACTC-3'; REV: 5'-CTAATGGGAACGTCACACACC-3.

Figure 8:
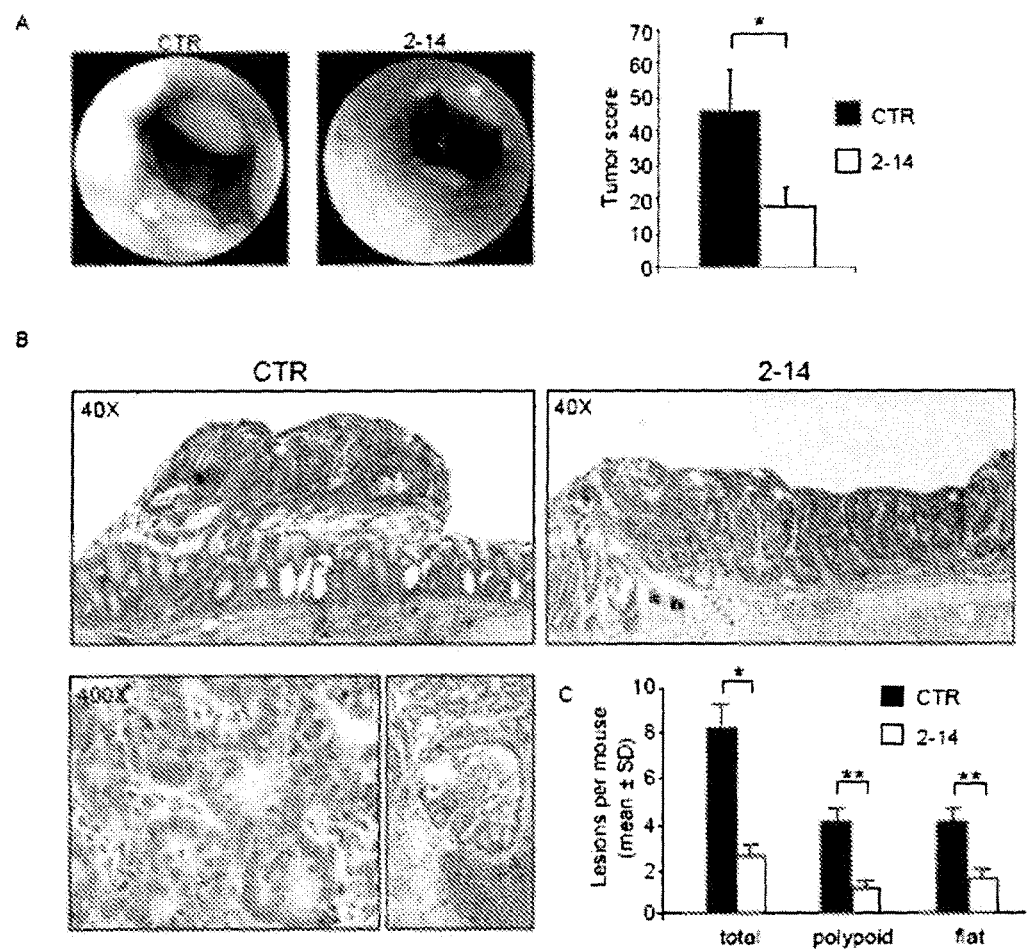
FIG. 8A are representative endoscopic pictures showing the development of colon tumors in mice treated with PBS (Ctr) or compound 14. Right inset shows endocscopic scoring of tumor development.
FIG. 8B are representative pictures of H&E stained colonic sections.
FIG. 8C depicts the effect of treatment on the multiplicity of neoplastic lesions.

Colonic sections were stained with hematoxylin and eosin (H&E). The degree of inflammation and the presence of neoplastic lesions were evaluated and graded by the same pathologist in a blinded fashion. Immunohistochemistry for PCNA was performed using a PCNA staining kit (ZYMED Laboratories, Carlsbad, Calif., U.S.A.) according to the manufacturer's instructions. Multiple colonic, flat and polypoid lesions were seen in mice receiving AOM/DSS; compound 14 significantly reduced both types of lesions (polypoid and flat lesions were counted (* P-0.001; **P=0.02; FIG. 8C depicts the effect of compound 14 treatment on the multiplicity of neoplastic lesions). FIG. 8A are representative endoscopic pictures showing the development of colon tumors in mice treated with PBS (Ctr) or compound 14. The right inset shows the endoscopic scoring of tumor development in mice either left untreated or treated with compound 14. Data indicate the mean±SD of all experiments in which at least 6 mice per group were considered (control vs compound 14-treated mice * P=0.03). FIG. 8B shows H&E-stained colon sections of mice either treated with PBS (control) or compound 14 (original magnification, ×40). A polypoid or flat lesion is seen in control and compound 14-treated mice respectively. Bottom left inset shows a representative H&E-stained colonic section containing a dysplastic area in a mouse treated with PBS (×400). Bottom right inset shows a neoplastic area infiltrating a colonic follicle in a mouse treated with PBS. Proliferating cell nuclear antigen (PCNA)-staining confirmed the anti-proliferative effect of compound 14 By contrast, there was no significant change in PCNA staining in the normal colonic mucosa of mice treated with compound 14 thus confirming that compound 14 does not substantially affect the growth of normal colonic cells.

Values are expressed as means±SD and analyzed using the Student t test. Statistical analysis of the changes in the body weights of the mice and size of the tumours was done using a $\chi 2$ test. Significance was defined as P values less than 0.05.

Example 4

Cell Proliferation-Breast

All reagents were from Sigma-Aldrich (Milan, Italy), unless specified. Compound 14 was dissolved as a 25 mM stock solution in culture medium. 4T1 cells, a 6-thioguanine-resistant cell line derived from a BALB/c mammary carcinoma which spontaneously metastasizes to both the lung and liver, were obtained by ATCC and maintained at 37° C. in a humidified atmosphere of 5% CO2 in Dulbecco's modified Eagle's Medium (DMEM) supplemented with 10% inactivated fetal bovine serum (FBS) and 1% penicillin-streptomycin. For cell growth assays, serum-starved 4T1 cells were labeled with carboxyfluorescein diacetate succinimidyl ester (CFSE) (Invitrogen, Milan Italy) at 37° C. for 30 minutes, and then treated with increasing doses of compound 14. After 24 hours, cells were incubated with 5 µg/ml of propidium iodide (PI) for 15 minutes, at 4° C. CFSE and/or PI-positive cells were determined by flow cytometry (Becton Dickinson, Milan, Italy)

Eight- to 10-week-old female Balb/c mice were used for the 4T1 syngeneic tumor model. 4T1 cells ($1 \times 10^5$ cells in 300 µl PBS 1×) were injected subcutaneously (s.c.) into the flank of mice, whose fur was shaved and depilated. Three groups of 8 mice each were implanted with 4T1. The first group received daily s.c. 300 µl PBS (control), the remaining groups were injected daily with compound 14 (8 mg/kg/mouse) s.c. or intraperitoneally (i.p.). Both compound 14 and PBS were administered starting on day 3. Mice were monitored over the time for weight loss and sacrificed at day 14. Tumors were photographed, and excised, and their mass calculated according to the following formula: ½×(short diameter)×(long diameter)×(height).

Spontaneous metastases were measured by adapting methods described previously by Pulaski and Ostrand-Rosenberg (Cancer Research 58, 1486-1493, 1998). 4T1 tumor cells ($1 \times 10^5$ cells in 100 µl 1×PBS) were injected s.c. in the abdominal mammary gland of 8-10 weeks old female Balb/c mice. Three days after 4T1 injection, mice received daily i.p. administration of compound 14 (8 mg/kg/mouse) or PBS (control). Mice were monitored over the time for weight loss and sacrificed at day 35. Lungs and liver were removed from each mouse, and treated as follows: liver samples were finely minced and digested with an enzyme solution containing 1×PBS, 0.01% BSA, 1 mg/ml hyaluronidase, and 1 mg/ml collagenase type I for 20 min at 37° C. on a platform rocker; lung samples were finely minced and digested with an enzyme cocktail containing 1×PBS, 1 mg/ml collagenase type IV and 10 units/ml elastase for 1 h at 4° C. on a rotating wheel. At the end, samples were filtered through 70 µm nylon cell strainers and washed three times with 1×PBS. The resulting cell preparations were resuspended and plated neat or serially diluted in 10-cm tissue culture dishes in 20 ml of medium containing 60 µM 6-thioguanine. Suspensions were incubated in 10% CO2-air atmosphere at 37° C. for clonogenic growth. 6-Thioguanine-resistant tumor cells formed foci within 10-14 days, at which time they were fixed with methanol and stained with 0.03% methylene blue for counting. Total colony-forming cells were calculated on a per-organ basis.

Figure 9:
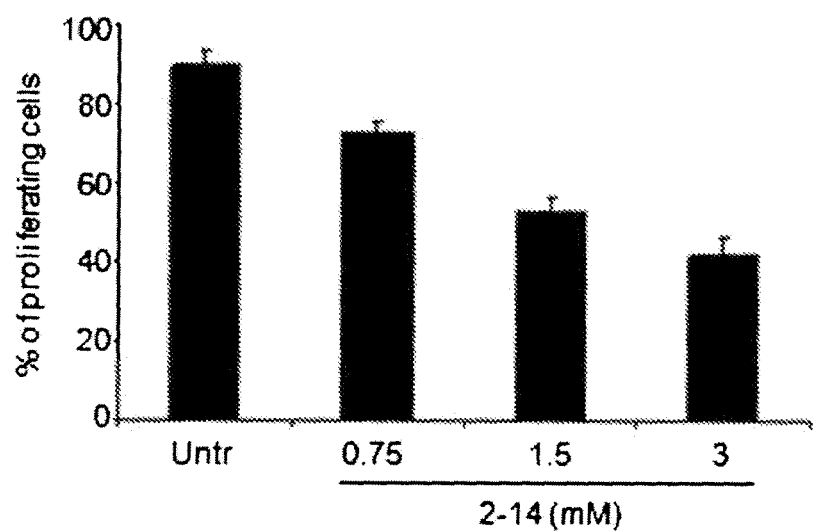
FIG. 9 depicts the inhibition the growth of 4T1 cells of compound 14. CFSE-labeled cells were either left untreated (Untr) or treated with graded doses of compound 14 for 24 hours and the percentage of proliferating cells evaluated by flow cytometry. Data indicate mean±SD of 3 experiments (* P=0.03, ** P<0.01)
Figure 10:
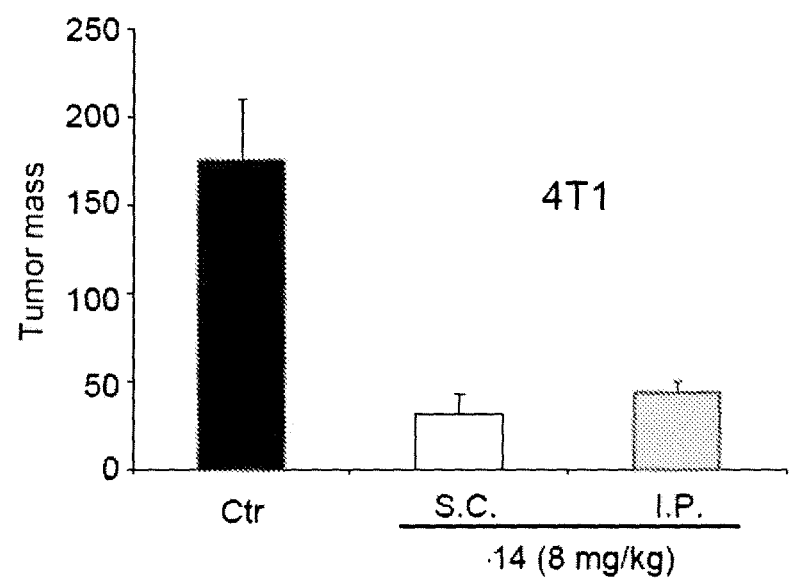
FIG. 10 depicts the reduction of the in vivo formation of 4T1-derived tumors. Representative photographic images of xenografts developed in control (ctr) and in compound 14-treated mice are shown at the bottom of the respective histograms (control vs compound 14-treated mice, * P<0.01).
Figure 10:
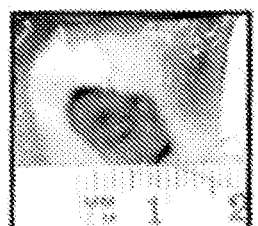
Figure 10:
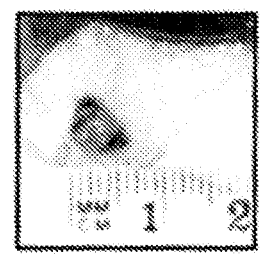

Compound 14 dose-dependently inhibited the in vitro proliferation of 4T1 cells (FIG. 9). Moreover, mice treated with compound 14 (4T1 cells were inoculated into Balb/c mice, and animals were then treated daily with subcutaneous or intraperitoneal administration of compound 14 (8 mg/kg/mouse) or PBS, starting 3 days after the 4T1 injection) exhibited a significant decrease in the 4T1-derived tumor mass in comparison to controls (FIG. 10). FIG. 10 indicates this effect was seen independently of the route of administration of compound 14.

Example 5

Figure 11:
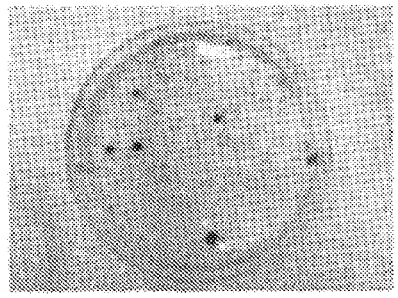
FIG. 11 depicts the reduction the in vivo formation of 4T1-derived metastasis using a disclosed compound. Representative photographic images showing 4T1 cells tumor foci derived from liver and lung homogenates of control (Ctr) and compound 14-treated mice.
Figure 11:
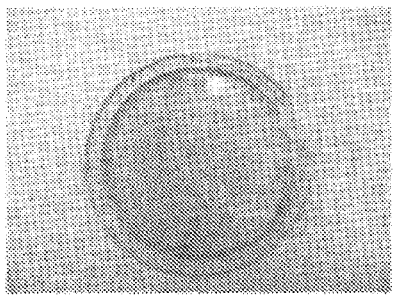
Figure 11:
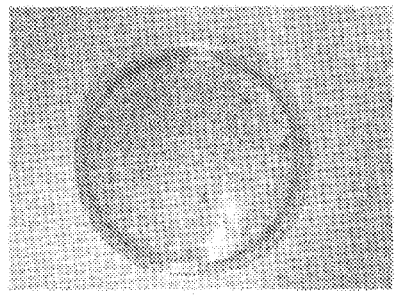
Figure 11:
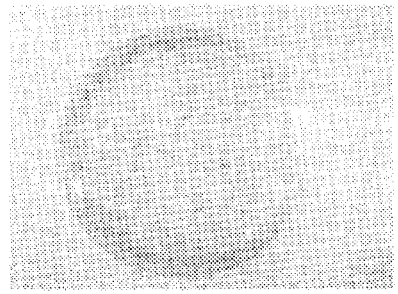

An in vivo model of mammary cancer metastasis induced by injection of 4T1 cells in the mammary gland of Balb/c mice is conducted. Compound 14-treated mice showed a reduction in the number of both lung and liver metastatic tumor cells as assessed by a clonogenic metastasis assay (FIG. 11). In this model, individual tumor cells form foci in culture and each focus represents and individual clonogenic tumor cell. The number of foci is therefore a direct measure of metastatic tumor cells per organ.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial
<220> FEATURE:
<223> OTHER INFORMATION: COX-2 forward primer

<400> SEQUENCE: 1
ttctttgccc agcacttcac                                                      20

<210> SEQ ID NO 2
<211> LENGTH: 20
<212> TYPE: DNA
<213> ORGANISM: Artificial
<220> FEATURE:
<223> OTHER INFORMATION: COX-2 reverse primer

<400> SEQUENCE: 2
ggatacacct ctccaccaat                                                      20

<210> SEQ ID NO 3
<211> LENGTH: 20
<212> TYPE: DNA
<213> ORGANISM: Artificial
<220> FEATURE:
<223> OTHER INFORMATION: TNF alpha forward primer

<400> SEQUENCE: 3
accctcacac tcagatcatc                                                      20

<210> SEQ ID NO 4
<211> LENGTH: 20
<212> TYPE: DNA
<213> ORGANISM: Artificial
<220> FEATURE:
<223> OTHER INFORMATION: TNF alpha reverse primer

<400> SEQUENCE: 4
gagtagacaa ggtacaaccc                                                      20

<210> SEQ ID NO 5
<211> LENGTH: 20
<212> TYPE: DNA
<213> ORGANISM: Artificial
<220> FEATURE:
<223> OTHER INFORMATION: IL-1 beta forward primer

<400> SEQUENCE: 5
tcaggcaggc agtatcactc                                                      20

<210> SEQ ID NO 6
<211> LENGTH: 21
<212> TYPE: DNA
<213> ORGANISM: Artificial
<220> FEATURE:
<223> OTHER INFORMATION: IL-1 beta reverse primer

<400> SEQUENCE: 6
ctaatgggaa cgtcacacac c                                                    21
``` indicated by the appended claims rather than by the foregoing description, and all changes that come within the meaning and range of equivalency of the claims are intended to be embraced therein.

We claim:

1. A method of inhibiting colon carcinogenesis comprising: administering to a patient at risk of colorectal cancer a pharmaceutical preparation comprising an agent represented by:

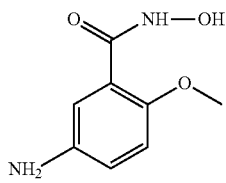

or pharmaceutically acceptable salts or stereoisomers thereof.

2. The method of claim 1, wherein the patient is human.

3. The method of claim 2, wherein the patient does not have detectable colorectal cancer.

4. The method of claim 1, wherein upon or before administration, spontaneous mutation frequency of colon carcinoma cells are present in the patient.

5. The method of claim 1, wherein the patient has Crohn's disease, inflammatory bowel disease, or ulcerative colitis.

6. A method for delaying clinical manifestation of colon adenocarcinoma in a patient at risk of colon cancer, comprising administering to the patient an effective amount of a compound of represented by:

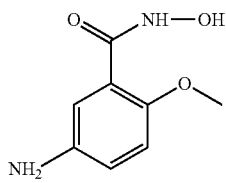

or pharmaceutically acceptable salts or stereoisomers thereof.

7. The method of claim 6, wherein the delay is at least 1 year as compared to a patient who is not administered the compound.

8. The method of claim 6, wherein the patient has at least about a 30% reduction of the mutation rate of colon carcinoma cells present in the patient.

9. The method of claim 6, wherein the patient is at higher risk of having the adenocarcinoma as compared to a general population.

10. The method of claim 9, wherein the patient has a genetically based risk.

11. The method of claim 6, wherein the compound is administered systemically.

12. The method of claim 6, wherein the compound is administered orally.

13. A composition suitable for systemic administration to a patient having a colorectal tumor, said composition comprising a compound represented by:

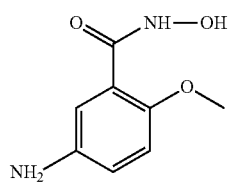

or pharmaceutically acceptable salts or stereoisomers thereof; and a pharmaceutically acceptable excipient; wherein the compound is present in an amount effective to inhibit the growth of the tumor when administered systemically.

14. The composition of claim 13, wherein the inhibition of growth of said tumor is measured as a delay in tumor doubling time.

15. The composition of claim 14, wherein the tumor doubling time is extended by a factor of two.

16. The composition of claim 15, wherein the inhibition of growth of said tumor is measured by a reduction in the volume of said tumor.

17. The composition of claim 16, wherein the volume of the tumor is reduced by at least 30%.

* * * * *